(12) United States Patent
Day et al.

(10) Patent No.: US 7,229,451 B2
(45) Date of Patent: *Jun. 12, 2007

(54) SKULL CLAMP WITH LOAD DISTRIBUTION INDICATORS

(75) Inventors: James L. Day, Cincinnati, OH (US); Donald A. Lincoln, Wrentham, MA (US)

(73) Assignee: Integra Ohio, Inc., Plainsboro, NJ (US)

( * ) Notice: Subject to any disclaimer, the term of this patent is extended or adjusted under 35 U.S.C. 154(b) by 78 days.

This patent is subject to a terminal disclaimer.

(21) Appl. No.: 10/687,857

(22) Filed: Oct. 17, 2003

(65) Prior Publication Data

US 2004/0097985 A1 May 20, 2004

Related U.S. Application Data

(63) Continuation of application No. PCT/US02/08829, filed on Mar. 21, 2002, which is a continuation of application No. 09/836,650, filed on Apr. 17, 2001, now Pat. No. 6,629,982.

(51) Int. Cl.
*A61B 19/00* (2006.01)

(52) U.S. Cl. .......................................... 606/130; 606/56
(58) Field of Classification Search .................. 606/130
See application file for complete search history.

(56) References Cited

U.S. PATENT DOCUMENTS

| | | | |
|---|---|---|---|
| 2,386,134 A | 10/1945 | Mermis | |
| 2,966,383 A | 12/1960 | Boetcker et al. | |
| 3,099,441 A | 7/1963 | Ries | |
| 3,457,922 A | * 7/1969 | Ray | 606/130 |
| 3,835,861 A | * 9/1974 | Kees et al. | 5/637 |
| 4,108,426 A | 8/1978 | Lindstroem et al. | |
| 4,169,478 A | * 10/1979 | Hickmann | 606/151 |
| 4,545,572 A | 10/1985 | Day | |
| 5,139,503 A | * 8/1992 | Salas-Ceniceros | 606/122 |
| 5,197,965 A | 3/1993 | Cherry et al. | |
| 5,254,079 A | * 10/1993 | Agbodoe et al. | 602/32 |
| 5,269,034 A | 12/1993 | Day et al. | |
| 5,276,927 A | 1/1994 | Day | |
| 5,537,704 A | 7/1996 | Dinkler | |
| 5,560,728 A | 10/1996 | McFadden | |
| D413,976 S | 9/1999 | Dinkler | |
| 6,629,982 B2 | 10/2003 | Day et al. | |

* cited by examiner

*Primary Examiner*—Anhtuan T. Nguyen
*Assistant Examiner*—Charles Sam
(74) *Attorney, Agent, or Firm*—Wood, Herron & Evans, LLP

(57) ABSTRACT

A three-pin skull clamp [10] includes a C-shaped frame [12] which partially encircles the head [18] of the patient, with a spring-loaded single skull pin assembly [22] located at one end of the frame [12] and adapted to engage the head [18] of the patient with a desired engagement force, and two spaced skull pins [30] mounted to a rocker arm [44] located at an opposite end of the frame [12]. Each of the rocker arm skull pins [30] resides in operative contact with an indicator cap [66] held by a spring-loaded pin carrier assembly [50], the indicator cap [66] being movable relative to the rest of the pin carrier assembly [50] in response to the engagement force applied to the corresponding skull pin [30] by the head [18] of the patient. By visibly comparing the positions of the indicator caps [66] relative to their respective pin carrier assemblies [50], one can readily determine whether the engagement forces are equally distributed between the two rocker arm skull pins [30]. If the indicator caps [66] show significantly unequal load distribution, the rocker arm [44] can be pivotally adjusted to produce a rocker arm orientation which results in a more equal load distribution on the two spaced rocker arm skull pins [30].

6 Claims, 2 Drawing Sheets

SKULL CLAMP WITH LOAD DISTRIBUTION INDICATORS

This application is a continuation of PCT Application Ser. No. PCT/US02/08829, filed on Mar. 21, 2002, and entitled "Skull Clamp With Load Distribution Indicators," which is currently pending, and which is a PCT/US continuation application claiming priority to previously filed U.S. application Ser. No. 09/836,650, filed on Apr. 17, 2001, and bearing the same title. The '650 application is now issued as U.S. Pat. No. 6,629,982 B2. Applicants respectfully claim priority to both of these prior U.S. applications via Title 35, USC, Section 120.

FIELD OF THE INVENTION

This invention relates to cranial stabilization products, and more particularly to a three pin skull clamp used to hold the head of a patient during surgery, most notably neurosurgery.

BACKGROUND OF THE INVENTION

Generally, the phrase "cranial stabilization" products or devices refers to a line of compatible and interconnectable medical devices used during neurosurgery to hold the head of a patient in a fixed position relative to a surgical operating table. A typical arrangement of such products may include, for example, a base unit which connects directly to the surgical table, one or more adaptors connected to the base unit, and a skull clamp connected to the adaptor the skull clamp having three skull pins which engage and hold the skull of the patient. The present assignee has commercialized a successive number of three pin skull clamps under the MAYFIELD® trademark. One particular skull clamp which has enjoyed significant market success for a long period of time is the three pin skull clamp shown and described in U.S. Pat. No. 4,169,478, entitled "Surgical Skull Clamp" which is expressly incorporated herein by reference in its entirety. The present invention relates to a three pin skull clamp similar to the one shown in the '478 patent.

As shown and described in the '478 patent, a three pin skull clamp includes a C-shaped frame defined by two legs which connect to each other via an adjustable ratchet mechanism, which adjusts to vary the space between the ends of the legs. The frame partially encircles the head of the patient, with the opposite ends of the legs residing on opposite sides of the head, in alignment with an imaginary axis through the head.

At an end of a first of the two legs of the C-shaped frame, the skull clamp has a single pin assembly, specially a threaded pin carrier and a single skull pin, oriented along the axis. This single pin assembly threadably connects to the end of the first leg, in alignment with the axis, and is threadably movable along the axis relative to the frame. This structure enables a surgeon to threadably move the single skull pin toward or away from the head of the patient. Preferably, the assembly is spring-loaded to provide some "give" for the single skull pin aligned along the axis and to enable measurement of the force applied by the single pin to the head of the patient. Generally, this force is in the range of about sixty to eighty pounds.

At the end of the other leg of the frame, on the opposite side of the head, two skull pins engage the head. These two skull pins are mounted in spaced relation to a rocker arm held at the end of the second leg. Preferably, the rocker arm is selectively rotatable about the axis, along with a swivel adaptor when not in a locked mode. When locked, the swivel adadtor is fixed relative to the frame and with respect to the axis. The mechanism for permitting this selective locking and unlocking, and consequently the nonrotation and rotation of the rocker arm and swivel adaptor about the axis relative to the frame, respectively, is disclosed and claimed in the aforementioned '478 patent. This mechanism forms no part of the present invention.

In addition to rotating about the axis with the swivel adaptor, the rocker arm is also pivotal about a pivot point relative to the swivel adaptor, to vary the respective distances between the rocker arm skull pins and the axis. Together the rotation of the rocker arm and the swivel adaptor, and the pivoting of the rocker arm relative to the swivel adaptor provide versatility in securing the three point skull clamp to the head, in a manner which assures consistently secure engagement of the skull in a fixed position during surgery.

Regardless of the adjustability of the rocker arm, with any three pin skull clamp the engagement forces at the rocker arm skull pins must be distributed equally, or at least close to equal. Otherwise, there is a possibility that the head of the patient will slip from engagement with the pins of the skull clamp, possibly resulting in serious injury to the patient. In many cases the single pin side is threadably moved so as to engage the skull of the patient with a desired amount of axial engagement force, and the head is securely held at the opposite end of the clamp by the two spaced pins mounted to the rocker arm. If the rocker arm is properly aligned on the head of the patient, the two rocker arm skull pins will be oriented at equal opposing angles relative to axis of the single pin, and the axial engagement load will be distributed evenly between the two rocker arm pins. For instance, if the single pin skull clamp is adjusted to achieve eighty pounds of force on the skull, and if the head is properly secured, there will be equal load distribution of the engagement force between the two rocker arm skull pins. Namely, this force for each of the rocker arm pins should be forty pounds multiplied by the cosine of the angle of the rocker arm pins relative to the single pin axis. This represents the normal load on each of the two rocker arm pins.

If the rocker arm is not properly aligned with the axis of the single pin, the normal load components on the two rocker arm pins will be unequal. Although it is not absolutely necessary for these engagement forces to be exactly equal, the stable holding of the head requires that those engagement forces be reasonably close to equal. Up to now assignee has not known of any practical way to determine with reasonable certainty whether there is an equal load distribution of the engagement forces at the rocker arm skull pins.

Although it has been fairly common to use the threaded pin assembly to measure the engagement force on the spring-loaded single pin at one end of the skull clamp, that same practice is neither practical nor desirable at the rocker arm end of the skull clamp. For one thing, mounting of a pair of similarly constructed threaded single pin assemblies to the opposite ends of the rocker arm would likely interfere with free rotation of the rocker arm and the swivel adaptor about the axis, when in the unlocked mode.

Also, the single pin assembly threadably adjusts relative to the first leg of the frame to enable the movement of a single pin to eventually cause head engagement by all three pins. It is neither desirable nor practical for the neurosurgeon or surgery room attendants to threadably adjust three separate skull pins in order to engage the head of the patient. Also, it is desirable to have the two spaced rocker arm skull pins at about the same distances from the axis, to facilitate the obtaining of equal distribution of the load. But if these two pins were separately adjustable it would be much more difficult to consistently determine if equal load distribution has been achieved.

It is therefore an object of the present invention to make it easier for surgeons and surgery, room attendants to determine that there is a sufficiently uniform load distribution on the two spaced skull pins at the rocker arm side of a three pin skull clamp.

It is another object to the present invention to facilitate the quick and easy detection of unequal load distribution between the two spaced skull pins mounted to the rocker arm of a three pin skull clamp.

It is still another object of the present invention to achieve these aforementioned benefits in a simple manner, and within the framework and structure of a well known and highly successful skull clamp of the type shown and described in the '478 patent.

SUMMARY OF THE INVENTION

The present invention achieves the above-stated objects via a skull clamp rocker arm adapted to hold, at each of its opposing ends, a skull pin carrier assembly which receives a removably inserted skull pin in operative contact with an indicator cap, the cap being movable relative to the rest of the carrier assembly in response to the head engagement force applied to the skull pin. Thus, the position of the indicator cap relative to the carrier assembly provides a visual indication of the force on the skull pin.

With identical pin carrier assemblies located at both ends of the rocker arm, the surgeon or other operating room attendants can easily determine the relative load distribution on the two rocker arm skull pins, by simply looking at and comparing the positions of the indicator caps associated with the two spaced pin carrier assemblies. For instance, if one indicator cap extends beyond its carrier assembly a greater distance than the other, then that corresponding rocker arm skull pin has a greater engagement force than the other skull pin, and the load is not equally distributed. Conversely, if there is no visual difference between the relative positions of the indicator caps with respect to their respective pin carrier assemblies, the neurosurgeon and the surgical room attendants can visually determine and assure themselves that the engagement forces at the rocker arm end of the skull clamp are distributed sufficiently equally between the two rocker arm skull pins. Additionally, because the pin carrier assembly of the present invention is relatively simple and fits within a rocker arm similar to the one known and described in the '478 patent, this invention represents a user friendly improvement to a well known, successful and already-existing device.

According to a preferred embodiment of the invention, each end of the rocker arm is machined to form a bore sized to threadably receive the pin carrier assembly, and particularly an externally threaded hollow adjustment screw which forms part of the assembly. A forward end of the adjustment screw extends completely through the bore. The carrier assembly further includes a piston which extends axially through the adjustment screw, an indicator cap held thereto at the outer end via a flathead screw, and an internal spring which holds the indicator cap in a normally retracted position within a recess at the outer end of the adjustment screw, so as to not extend beyond the outer end of the adjustment screw of the pin carrier assembly. The adjustment screw threadably extends through the internally threaded bore in the rocker arm, to a desired distance which may be determined by visual markings on the adjustment screw, or simply by visual comparison.

A skull pin removably inserts within a forward end of the hollow adjustment screw. More specifically, the skull pin base, or encasement, located at its non-contact end, extends into the adjustment screw, in surface contact with an enlarged head end of the piston. Since the piston connects directly to the indicator cap, this places the skull pin in operative contact with the indicator cap.

The internal spring surrounds the piston. One end of the spring engages the head of the piston, while the other end engages an internal surface of the adjustment screw. The force of the spring retains the indicator cap within the adjustment screw recess, unless and until a predetermined engagement force is applied to the skull pin. Notably, it is not necessary to know the exact engagement force of the pins to the skull. However, for accurate comparison purposes it is important that the retainer force for holding each of the indicator caps within their respective recesses be identical, or as close to identical as possible. Otherwise, without equal retainer forces movement of the indicator caps relative to their respective pin carrier assemblies would not provide a meaningful comparison of load distribution on the corresponding skull pins. Preferably, this equal retainer force is done by using the same size, spacing and structure for the two pin carrier assemblies, but it is to be understood there are also other ways to assure equal retainer forces.

These and other features of the present invention will be more readily understood in view of the following detailed description and the drawings.

DETAILED DESCRIPTION OF THE INVENTION

Figure 1:
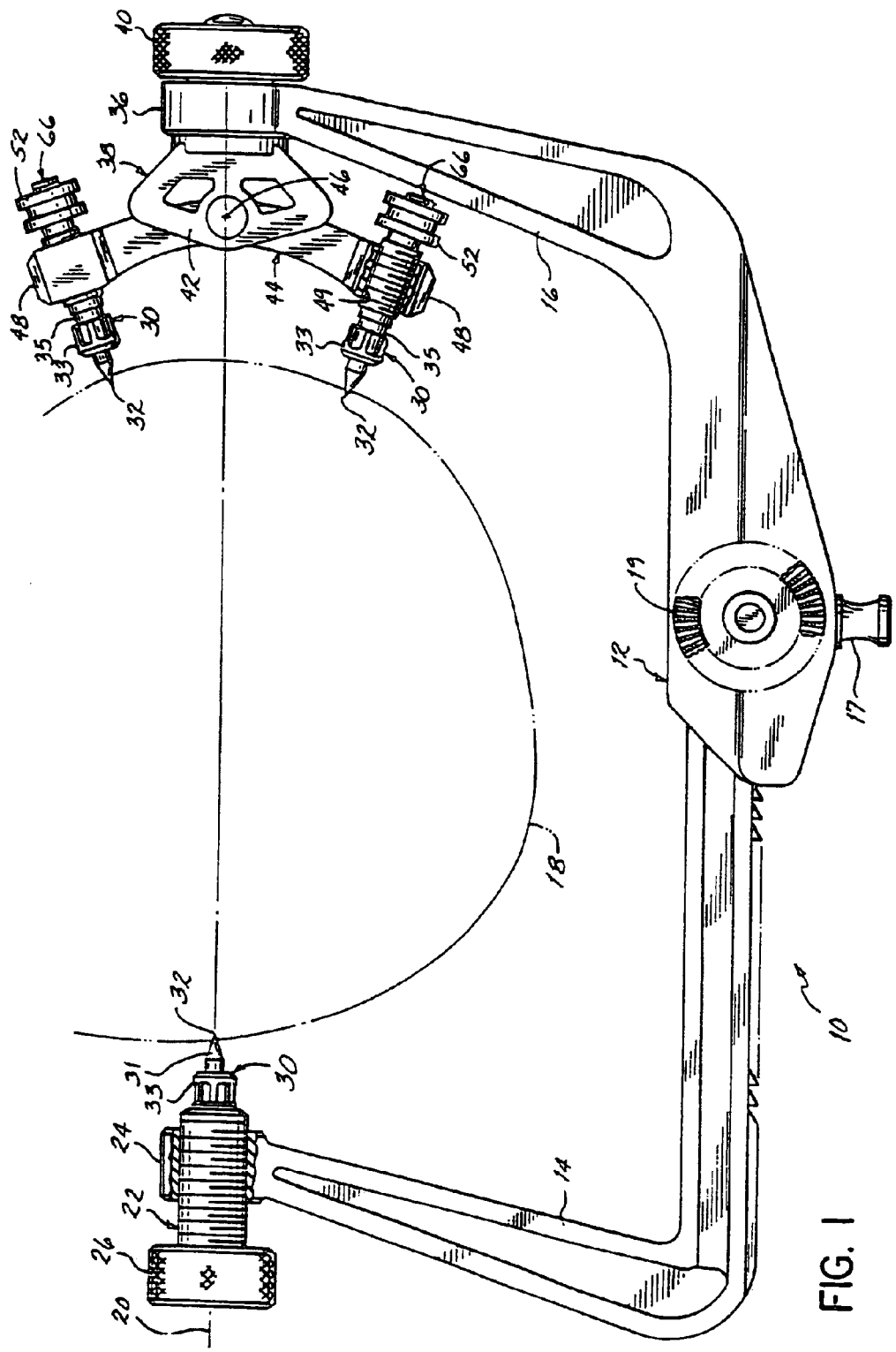
FIG. 1 is plan view of a skull clamp constructed in accordance with a first preferred embodiment of the invention.

FIG. 1 shows, in plan view a skull clamp 10 constructed in accordance with a first preferred embodiment of the invention. As noted previously, the skull clamp 10 is similar to the skull clamp shown and described in U.S. Pat. No. 4,169,478, which is also owned by the assignee of the present application. The skull clamp 10 includes a generally C-shaped frame 12 formed by a first leg 14 and a second leg 16. More specifically, FIG. 1 shows the first leg 14 interconnected to the second leg 16, with the spacing between the legs 14 and 16 determined by a pin and ratchet mechanism 17. The second leg 16 includes a starburst surface finish 19 to enable the skull clamp 10 to be securely fastened to another cranial stabilization device, such as an adaptor, (not shown) as is well known in the field of cranial stabilization. The C-shaped frame 12 of skull clamp 10 partially encircles, or encompasses, the head of a patient. In FIG. 1 the head is shown in phantom via reference numeral 18. When the skull clamp 10 is secured to the head 18, the outer ends of the legs 14 and 16 are aligned along an imaginary axis 20 which also extends through the head 18.

A threaded single pin assembly 22 resides at an outer end 24 of the first leg 14. This threaded single pin assembly 22 includes a rotatable knob 26 which causes relative movement of the assembly 22 along axis 20 via a threadable engagement with the frame leg 14. More specifically, rotation of knob 26 moves a corresponding skull pin 30, which is held by assembly 22, along axis 20 toward or away from the head 18. The skull pin 30 includes a forward metal section 31 which terminates at a point 32 at its forward or contact end, and a base, or encasement section located at the outer end. The skull pin 30 may be reusable or disposable and is preferably of the type shown in U.S. Pat. No. 5,197,965, entitled "Skull Clamp Pin Assembly," which is expressly incorporated by reference herein, in its entirety. That is, the base section of the pin 30 has an enlarged outer section 33 and a reduced size section 35. Preferably, the single pin assembly 22 includes an internal spring, with the spring force set to indicate when a predetermined engagement force is achieved between the pin 30 and the head 18.

At the opposite end of the skull clamp 10, at the outer end 36 of the second leg 16, a rocker arm assembly 38 is aligned along the axis 20 to hold the opposite end of the head 18. The rocker arm assembly 38 includes an outer knob 40 which connects to a swivel adaptor bracket 42 and a rocker arm 44. The swivel adaptor bracket 42 and the rocker arm 44 are rotatable about axis 20 when the knob 40 is rotated relative to second leg 16 to an "unlocked" position. Conversely, swivel adaptor bracket 42 and rocker arm 44 are fixed relative to axis 20 when the knob 40 is rotated to a "locked" position. The details of this locking and unlocking feature at the rocker arm end of a three pin skull clamp are shown and described in more detail in the '478 patent, and form no part of the present invention.

The rocker arm 44 also pivots relative to the swivel adaptor bracket 42, via a bolted connection about pivot point 46. However, this pivotal movement is not free and easy, but requires some force to be applied to one of the outer ends 48 of the rocker arm relative to the other end. This pivotal feature is not shown and described in the '148 patent, but was developed subsequently to that invention. Nevertheless, it also forms no part of the present invention.

Figure 2:
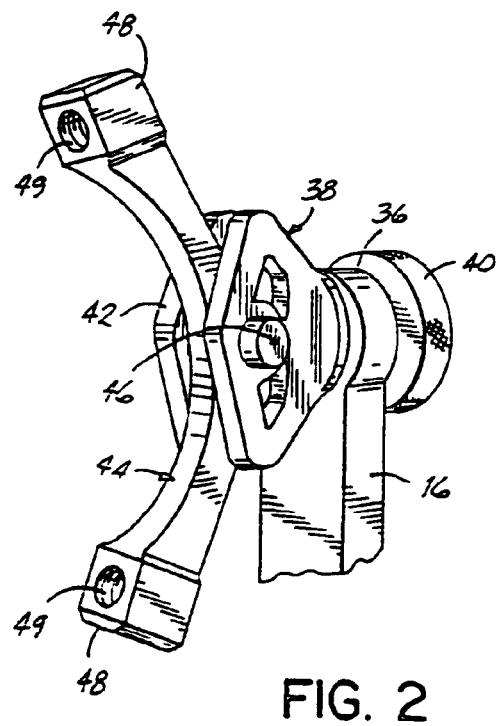
FIG. 2 is a perspective view of the rocker arm end of the skull clamp of FIG. 1, without the rocker arm pins or their corresponding pin carrier assemblies.

Each of the outer ends 48 of the rocker arm 44 is enlarged, and includes an outer shape which is generally square in cross-section, and has an internally threaded bore 49 extending therethrough. This structure is shown more clearly in FIG. 2. Each of these internally threaded bores 49 is sized to receive an externally threaded pin carrier assembly 50 which extends completely therethrough. Because the pin carrier assemblies 50 are identical, only one is described.

Figure 4:
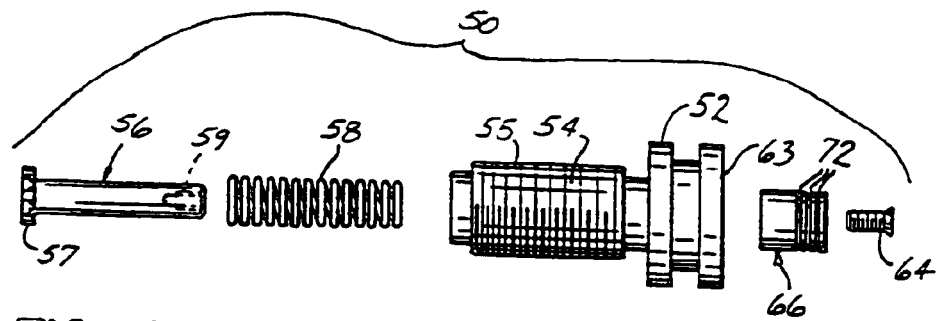
FIG. 4 is an exploded view of the pin carrier assembly of FIG. 3.
Figure 3:
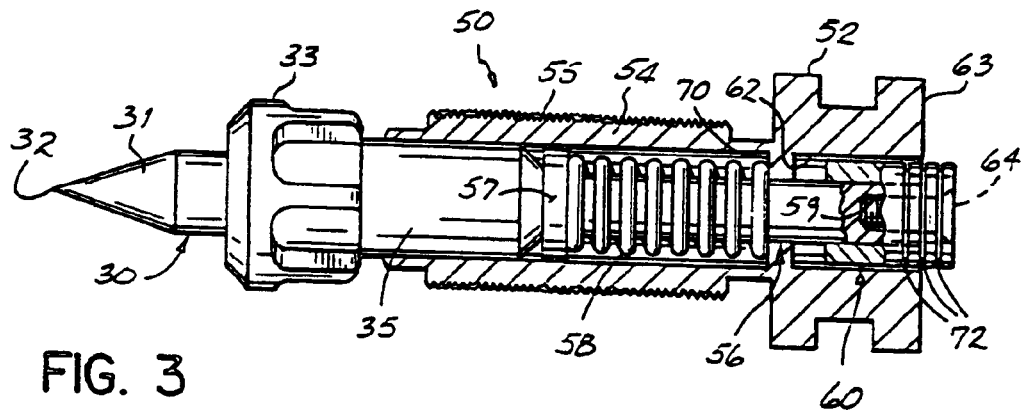
FIG. 3 is a longitudinal view, in partial cross section, of one of the pin carrier assemblies shown on the skull clamp of FIG. 1, with the skull pin inserted therein.

FIGS. 3 and 4 show the pin carrier assembly 50 in more detail, in longitudinal cross-section, with a skull pin 30 (not shown in cross-section) residing therein in FIG. 3. The pin carrier assembly 50 includes an outer end head or handle 52 which facilitates threadable insertion within the bore 49 at the outer end 48 of the rocker arm 44. More specifically, the handle 52 is located at the outer end of a hollow adjustment screw 54 which has external threads 55 formed thereon. These external threads 55 correspond in size to the internal threads of the bore 49 in the rocker arm 44. The adjustment screw 54 is hollow, and when threadably inserted extends completely through the outer end 48 of the rocker arm 44 to a desired distant.

A piston 56 resides within the hollow adjustment screw and includes an enlarged head 57 located at a first or forward end, and an internally threaded hole 59 located at a second, opposite end. The second end of the piston 56 extends into a recess 62 formed in the outer surface 63 of the handle 52, and a flathead screw 64 threads into the threaded hole 59 to capture an indicator cap 66 at the second end of the piston 56. An internal spring 58 surrounds the piston 56, with one end engaging the enlarged head 57 and an opposite end engaging an internal surface 70 of the adjustment screw 54. The force of the spring 58 pushes the enlarged head 57 of the piston 56 away from the inner surface 70 (to the left in FIG. 3), thereby holding the indicator cap 66 completely within the recess 62. The indicator cap 66 preferably includes one or more parallel markings 72 to facilitate visual detection of the distance the indicator cap 66 has moved outwardly from the recess 62 relative to handle 52. Such movement may occur when engagement force from the head 18 is transferred via the pin 30 to the piston 56. More specifically, the inserted section 35 of the pin 30 resides in contact with the piston 56. Thus, the inserted skull pin 30 resides in operative contact with the indicator cap 66.

Both outer ends 48 of the rocker arm 44 include identical pin carrier assemblies 50. Thus, when the engagement forces at second end 36 are uniformly distributed between the skull pins 30 held by the rocker arm 44, the indicator caps 66 should be in the same positions relative to their respective outer ends 52 of their pin carrier assemblies 50. On the other hand, if one indicator cap 66 has moved beyond its respective recess 62 a distance which differs from the movement at the other indicator cap 66, then the neurosurgeon or appropriate operating room attendants can easily determine that there are unequal normal loads on the pins 30 at the rocker arm 44 end of the skull clamp 10. If the loads are too unequal the rocker arm 44 can be adjusted slightly about pivot point 46 to create a more equal load distribution. In some rare cases, the knob 40 may need to be turned to the unlocked position, to rotate the swivel adaptor bracket 42 and to reposition the rocker arm 44 to a different location relative to the head 18. However, it is generally undesirable to do this, because it would create different surgical contact points for the head 18.

The present invention is not designed to identify the specific amount of engagement force between the head 18 and each of the two pins 30 located on the rocker arm 44. The magnitude of the engagement forces on the single pin side of the skull clamp will be known, within a reasonable amount of certainty, and the force vectors for the pins 30 on the rocker arm 44 will, when combined equal, i.e. counteract, the engagement force from the single pin side. Thus, it is not necessary to know actual forces on the rocker arm pins. It is only necessary to assure that the engagement forces on the rocker arm pins are equally distributed, or at least sufficiently close to being equally distributed to provide secure holding of the head 18 of the patient during surgery.

In use, the skull clamp 10 of the present invention is assembled and used in the same manner as is well known in the cranial stabilization field. Prior to use the pin carrier assemblies 50 are threaded into the outer ends 48 of the rocker arm 44, to a desired distance. This distance can be indicated visibly by the distance that the adjustment screws 54 extend beyond or into the square shaped ends 48 of the rocker arms 44. Prior to threaded connection of the pin carrier assembly 50, the spring 58 is placed on the piston 56, the piston 56 is extended within the adjustment screw 54 so that the hole 59 is located in the recess 62. The indicator cap 66 is placed on the outer end of the piston 56, and the flathead screw 64 is threadably inserted into the hole 59 to capture the indicator cap 66. The force of the spring 58 holds the enlarged head 57 away from the outer end 52 of the pin carrier assembly 50, so that the indicator cap 66 resides completely within the recess 62.

To use the skull clamp 10, one skull pin 30 is inserted into the single pin assembly 22, and two pins 30 are inserted into the hollow forward ends of the adjustment screws 54 located at opposite ends 48 of the rocker arm 44, so that the smaller sections 35 of the pins 30 contact the enlarged heads 57 of the pistons 56. When the skull clamp 10 is placed on the head 18 of a patient and all three pins 30 are oriented at about the desired locations for securement to the head 18, the knob 26 is adjusted to move the single skull pin 30 on leg 14 into contact with the head 18 to supply the desired engagement force. Typically this engagement force is in the range of sixty to eighty pounds. This causes the other two pins 30 on the rocker arm 44 also to engage the head 18 with sufficient holdings force.

If this engagement force is uniformly distributed between the two skull pins 30 at the rocker arm 44, then both indicator caps 66 will be in the same position relative to their respective outer ends 52. Depending upon the force of the spring 58, this may mean that the indicator caps 66 remain within their recesses 62. On the other hand, with lower spring forces, both indicator caps 66 could extend beyond the respective outer ends 52, perhaps a distance equal to one of the markings 72. By comparing the positions of the two indicator caps 66 relative to the outer ends 52, the neurosurgeon or operating room personnel can readily compare the force distribution on the skull pins 30 mounted to the rocker arm 44.

While the present application describes a preferred embodiment of the invention, it is to be understood that variations may be made thereto without departing from the scope of the invention. For instance, those skilled in the art will appreciate that the particular structural details shown and described could be varied to achieve the same visual comparison of load distribution at the two spaced rocker arm pins. Therefore, the inventors do not intend this detailed description to be limiting relative to interpretation of the following claims, but rather exemplary of the presently preferred embodiment.

We claim:

1. A skull clamp for rigidly holding the skull of the patient during surgery comprising:

a C-shaped frame to partially encircle the head of the patient, the frame having first and second ends adapted to be located on opposite sides of the skull of the patient;

a pin assembly located at a first end of the frame and oriented in alignment with an axis which, when in use, extends through the head of the patient and through the second leg of the C-shaped frame, said assembly holding a single skull pin and being adjustable relative to the first end of the frame to enable an operator to selectively determine the force applied to the skull of the patient by the corresponding single skull pin;

a rocker arm located at a second end of the frame, the first and second ends of the frame being aligined along an axis bisecting the skull of the patient and the rocker arm being rotatable relative to the axis; and a pair of spaced skull pins mounted in a spaced relation on the rocker arm and adapted to engage and hold the skull of the patient opposite the single skull pin, each of said pair of spaced skull pins operatively contacting an indicator, each of the indicators being movable in non-alignment with the axis and relative to the respective spaced skull pin along a direction parallel to the orientation of the respective spaced skull pin in response to the engagement force applied by the skull of the patient to the respective spaced skull pin, thereby to provide an indication of the load distribution of the engagement forces on said pair of spaced skull pins.

2. The skull clamp of claim 1 wherein each of said pair of skull pins resides within a bore located at an end of the rocker arm, and further comprising:

a pair of pin carrier assemblies, each pin carrier assembly held within the bore and holding the respective indicator in operative contact with the respective skull pin.

3. The skull clamp of claim 2 wherein each of the two pin carrier assemblies further comprises:

a spring biasing the respective indicator in a desired position relative to the frame, so that the indicator moves relative to the frame in response to force on the skull pin only after the force of the spring is overcome.

4. The skull clamp of claim 3 wherein each indicator includes markings to facilitate visual detection of the movement of the indicator relative to the frame, thereby to facilitate comparison of the load distribution between said pair of spaced skull pins.

5. A skull fixation device comprising:

a frame adapted to partially encircle the skull of a patient, the frame having at least one leg which is adapted to be located adjacent the skull when the fixation device is in use, the at least one leg being aligned substantially perpendicular to an axis which extends through the skull; and a pair of spaced skull pins mounted in spaced relation on a swivel bracket located at said at least one leg of the frame, the pair of spaced skull pins being spaced from the axis and adapted to engage and hold the skull of the patient, each of the pair of spaced skull pins operatively contacting a respective indicator, the indicators being spaced from the axis and movable relative to the swivel bracket in response to the force applied by the skull to the respective skull pin, thereby to indicate the load distribution of the forces on the spaced skull pins, wherein the swivel bracket is rotatable about the axis to facilitate placement of the pair of spaced skull pins in desired positions relative to the skull, and the swivel bracket remains a fixed distance, along the axis, from said at least one leg of the frame.

6. The skull fixation device of claim 5 and further comprising another leg forming part of the frame, and a third pin mounted to said another leg and oriented along the axis.

* * * * *

UNITED STATES PATENT AND TRADEMARK OFFICE
CERTIFICATE OF CORRECTION

| | | |
|---|---|---|
| PATENT NO. | : 7,229,451 B2 | Page 1 of 1 |
| APPLICATION NO. | : 10/687857 | |
| DATED | : June 12, 2007 | |
| INVENTOR(S) | : James L. Day and Donald A. Lincoln | |

It is certified that error appears in the above-identified patent and that said Letters Patent is hereby corrected as shown below:

Col. 1, lines approx. 29-30, reads "connected to the adaptor the skull clamp" and should read --connected to the adaptor, the skull clamp--.

Col. 3, line 7, reads "easier for the surgeon and the surgery, room attendants to" and should read --easier for the surgeon and the surgery room attendants to--.

Col. 4, line 35, reads "FIG. 1 is plan view of" and should read --FIG. 1 is a plan view of--.

Col. 4, lines 63-64, reads "such as an adaptor, (not shown) as is well known" and should read --such as an adaptor (not shown), as known--.

Col. 5, line 42, reads "described in the '148 patent," and should read --described n the '478 patent--.

Col. 5, line 65, reads "a desired distant." and should read --a desired distance.--.

Col. 7, last line, reads "being aligined along an" and should read --being aligned along an--.

Signed and Sealed this

Eighteenth Day of December, 2007

JON W. DUDAS
*Director of the United States Patent and Trademark Office*